(12) United States Patent  
Miller et al.

(10) Patent No.: US 7,785,578 B2  
(45) Date of Patent: Aug. 31, 2010

(54) NON-INVASIVE OCULAR DRUG DELIVERY

(75) Inventors: David J. Miller, Bountiful, UT (US); S. Kevin Li, Salt Lake City, UT (US); William Higuchi, Salt Lake City, UT (US)

(73) Assignee: Aciont, Inc., Salt Lake City, UT (US)

(*) Notice: Subject to any disclaimer, the term of this patent is extended or adjusted under 35 U.S.C. 154(b) by 1266 days.

(21) Appl. No.: 10/269,911

(22) Filed: Oct. 11, 2002

(65) Prior Publication Data

US 2004/0071761 A1    Apr. 15, 2004

(51) Int. Cl.
*A61K 31/74* (2006.01)
(52) U.S. Cl. .................................... 424/78.04
(58) Field of Classification Search ............... 424/427, 424/450, 489, 78.04
See application file for complete search history.

(56) References Cited

U.S. PATENT DOCUMENTS 6,410,046 B1 *  6/2002  Lerner ..................... 424/434

OTHER PUBLICATIONS

Lallemand et al, Cyclosprine A Delivery to the Eye: A Pharmaceutical Challenge, European Journal of Pharmaceutics and Biopharmaceutics, vol. 56, Issue 3, Nov. 2003, pp. 307-318.*

Kaur et al, Vesiclar Systems in Ocular Drug Delivery: An Overview' International Journal of Pharmaceutics, vol. 269, Issue 1, Jan. 9, 2004, pp. 1-14.*

* cited by examiner

*Primary Examiner*—Carlos A Azpuru
(74) *Attorney, Agent, or Firm*—Thorpe North & Western LLP

(57) ABSTRACT

The present invention is drawn to a pharmaceutical compound for the treatment of posterior retinal diseases through topical application of the compound. The compound includes an effective amount of a therapeutic compound, and at least one additional agent that helps to prolong the residence time of the therapeutic compound within the extraocular space, or increase the transport of the therapeutic compound across a tissue of an eye toward and into a posterior ocular region, or both. The invention is additionally drawn to a device and method for delivering the compound.

16 Claims, 3 Drawing Sheets

NON-INVASIVE OCULAR DRUG DELIVERY

BACKGROUND OF THE INVENTION

1. Field of the Invention

The present invention generally applies to the treatment of ocular conditions, and specifically applies to improved methods, materials and devices for the non-invasive treatment of intermediate and posterior eye pathologies.

2. Background Art

Numerous sight-threatening maladies result from diseases in the posterior portion of the eye. Posterior and intermediate uveitis, HSV retinitis, age related macular degeneration, diabetic retinopathy, bacterial, fungal, or viral endophthalmitis, eye cancers, glioblastomas, and glaucomatous degradation of the optic nerve are but a few of the diseases that will result in blindness if left untreated.

A plethora of conventional pharmacological agents currently exist to treat these conditions. Delivery of the agents to the site of action, however, has heretofore proven difficult. In order to exert a sufficient pharmaceutical effect on the intermediate and posterior eye tissues, the compound must be delivered to these tissues in pharmacologically relevant concentrations. Delivering therapeutic concentration of drug to the intermediate and posterior ocular region via conventional delivery methods has proven difficult in practice, as the methods are fraught with drawbacks.

Currently, there are four known methods of delivering the compounds to the posterior ocular chamber including: direct injection into the vitreous, systemic administration with subsequent distribution into the eye through optic blood flow, injection into the areas surrounding the globe with subsequent passive diffusion through the sclera into the globe, and topical application to the cornea and/or sclera with subsequent passive diffusion posteriorly into the globe's interior. Each of the above-mentioned methods has its shortcomings.

The preferred delivery method for drug administration into any body tissue is by oral administration due to its simplicity, non-invasiveness, and patient acceptance. Less acceptable, but effective methods of reaching body tissues by way of the systemic vasculature include invasive transcutaneous injections of compounds through the skin. Yet other methods involve non-invasive transport by percutaneous absorption. Generally, however, delivery of a drug into the eye via systemic methods is difficult because the eye is an immunoprivileged organ. The blood vessels supplying the eye have tight junctions between their endothelial cells, thus preventing the transfer of most non-endogenous compounds from the blood to the eye. In this way, the blood-retinal barrier's function is very similar to the protection afforded the central nervous system by the blood-brain barrier. The blood-retinal barrier inhibits entry of most systemically circulating drugs into the eye itself. In order to achieve therapeutic concentrations in the eye following systemic delivery, therefore, large quantities of the drug must be administered to overcome the barrier. The excessive quantities of the drug in the systemic circulation, of course, expose the entire body to the negative effects and potential toxicity of the drugs. For example, if a steroid is administered in large doses to a patient, such as for the treatment of uveitis, the entire body experiences the steroidal effects. These effects include fluid retention, electrolyte imbalance, immunosuppression, myopathy, cataract formation, behavior changes and bone demineralization, among others. Similarly, if large doses of a vascular endothelial growth factor (VEGF) antagonist are administered, systemic effects include the delayed healing of injuries and decreased blood perfusion to body tissues. As such, whole body toxicity precludes systemic delivery of medicaments as a way to achieve therapeutic concentration in the globe's interior.

More targeted, non-systemic delivery methods are similarly known in the art. As early as the 1920's, clinicians administered drugs to the eye by retrobulbar injection. Other methods have developed through the years, including sub-tenon's capsule, peribulbar, and subconjunctival injections, all of which comprise invasive delivery methods for injecting large amounts of a drug into a periocular space. Through injection to areas surrounding the globe, these methods achieve a high local concentration of the drug, allowing for transcleral drug delivery to the posterior chamber by passive, Fickian driven diffusion. The injections, however, carry significant risks, including pain, risk of infection, tissue scarring, retrobulbar hemorrhage, ecchymosis, elevated intraocular pressure, accidental perforation of the globe, and eye proptosis. Further, despite their relatively targeted nature, periocular injections can result in high systemic drug concentrations because the drug does not diffuse unidirectionally into the globe, but diffuses radially into the capillaries and vasculature surrounding the globe. In fact, some researchers found systemic levels of 60 ng/ml plasma following a 5 mg peribulbar injection of dexamethasone; a plasma concentration they concluded was comparable to a "high oral dose" (approximately 7.5 mg). Weijtens O, Van Der Sluijs F A, Schoemaker R C, Lentjes EGWM, Choen A F, Romijn FPHTM, and Van Meurs J C (1997). *Peribulbar corticosteroid injection: vitreal and serum concentrations after dexamethasone disodium phosphate injection*. Am J Ophthalmol, 123:358-63.

Another method for the introduction of medicament into the eye includes direct injection of the drug into the vitreous. Intravitreal injections have been used to deliver antibacterial and antifungal agents for the treatment of bacterial and fungal endophthalmitis, antivirals for treatment of viral retinitis, and steroids for the treatment of uveitis. The half-life of most compounds in the vitreous, however, is relatively short, usually on the scale of just a few hours. Therefore, the intravitreal injections must be repeated, often multiple times a week. The repeated injections can cause pain, discomfort, intraocular pressure increases, intraocular bleeding, increased chances for infection, and the possibility of retinal detachment.

A similar method to the intravitreal injections requires the implantation of drug containment matrices into the vitreal compartment or the surgical implantation of a sustained release drug delivery device into the vitreal compartment. Such devices may be bioerodible, or non-erodible. They often must be, however, surgically implanted into the interior of the globe to be effective. Once the drug payload is exhausted, a new matrix may be inserted to replace the old, or the old device left in place and a new matrix inserted nearby. Although effective, such devices carry with them significant risks, separate and apart from the risks associated with major implantation surgery. The problems include pain, discomfort, intraocular bleeding, intraocular pressure increases, chance of infection, and the possibility of retinal detachment. Lastly, if ocular drug toxicity is observed, such as increased intraocular pressure or cataractogenesis during implantation therapy, the toxicity has to be managed or the device removed.

One final category of drug delivery includes the introduction of materials into the interior of the ocular globe by diffusion through the sclera into the globe's interior. Such diffusion can be passive or active, wherein drug may be driven by an external driving force, such as iontophoresis, into the eye.

For passive delivery of drugs to the eye, a sustained release drug delivery device, a matrix saturated with the drug, a polymer containing the drug, or a collagen shield containing the drug can all be placed adjacent to the episclera. The drug, once in contact with the eye, diffuses into the ocular tissue by a process that is governed by Fick's law. Fick's law reads:

$$J=PA\Delta C$$

Where
J=drug flux into the eye
P=permeability of drug through the sclera
A=area of device in contact with the eye
ΔC=concentration gradient across the sclera Despite the well-known nature of Fickian transport, it has not as of yet been recognized that passive delivery through the conjunctiva and sclera could yield therapeutic concentrations of medicament in the posterior portion of the eye. The inability to deliver effective amounts of drug to the eye runs contrary to empirically determined information on the transport of those drugs.

Geroski and Edelhauser investigated the in vitro passive scleral permeability of numerous compounds. Geroski, D. H. and H. F. Edelhauser, *Transscleral drug delivery for posterior segment disease*, Adv. Drug. Del. Rev. 52:37-48 (2001). Through their results, Geroski and Edelhauser found that permeability of the compounds was inversely related to molecular weight, with smaller compounds having higher transport rates than larger compounds. Regardless of molecular size, however, the transport rates of all compounds remained relatively high, with small compounds having transport rates on the order of $1\times10^{-5}$ cm/s, and large compounds having transport rates on the order of $1\times10^{-6}$ cm/s. Yet despite finding such high permeabilities, Geroski and Edelhauser failed to recognize the reasonable utility of in vivo passive, transscleral drug delivery to achieve therapeutic drug concentrations within the eye.

Thus, the inability to deliver drugs effectively through topical administration must be due to environmental conditions in the drug delivery pathway or within the eye itself that degrade or eliminate the drug. Two particular conditions have been postulated as being responsible for the loss of topically administered drug. Topically administered drugs are exposed directly to lacrimal fluids within the eye, which contain enzymes and proteins that can attack the drug. It is postulated that, once applied, enzymes, which break the drug down from its effective form, attack the drugs. Alternately, the lacrimal proteins can bind with the active form of the drug, thereby inactivating it or preventing its transport. In any case, the environmental conditions in the extrascleral space, within the transport pathways, and within the eye tend to create a harsh environment for the transport and viability of the effective form of the drug.

As mentioned, one reason why conventional topical administration of drugs to the eye has heretofore not achieved effective concentrations of drug in the posterior of the eye is because of the effectiveness of the vasculature in clearing the drug. In order for topically administered compounds to be reach the back of the eye, the drug must pass through several layers of ocular tissues before reaching the vitreous. Several of theses tissues, more specifically the conjunctiva and the choroid, have extensive blood supplies. In addition to delivering nutrients and oxygen to the tissues, these vascular beds are also responsible for removing waste byproducts of metabolism. Further, these vascular beds serve a protective function by removing exogenous and potentially noxious stimuli before they can reach the visual pathways of the eye's interior. These tissues contain the clearing vasculature of the eye, which can shunt the drug from the ocular region to the systemic vasculature, thus not allowing the drug to be exposed to the back of the eye. Combined with enzymatic degradation and protein binding elucidated above, these environmental conditions create a particularly formidable barrier for delivery to the posterior portion of the eye following passive, topical delivery.

As such, it is an object of the present invention to effectively and safely deliver medicament to a posterior retinal portion of an eye, without the potential risks and side effects associated with systemic and injectable delivery methods.

It is another object of the present invention to provide for an enhanced pharmaceutical preparation that improves the effective delivery concentration of a medicament to the intermediate and posterior retinal region.

These and other objects will become apparent to one of ordinary skill in the art given the specification, claims and drawings appended hereto.

SUMMARY OF THE INVENTION

Figure 1:
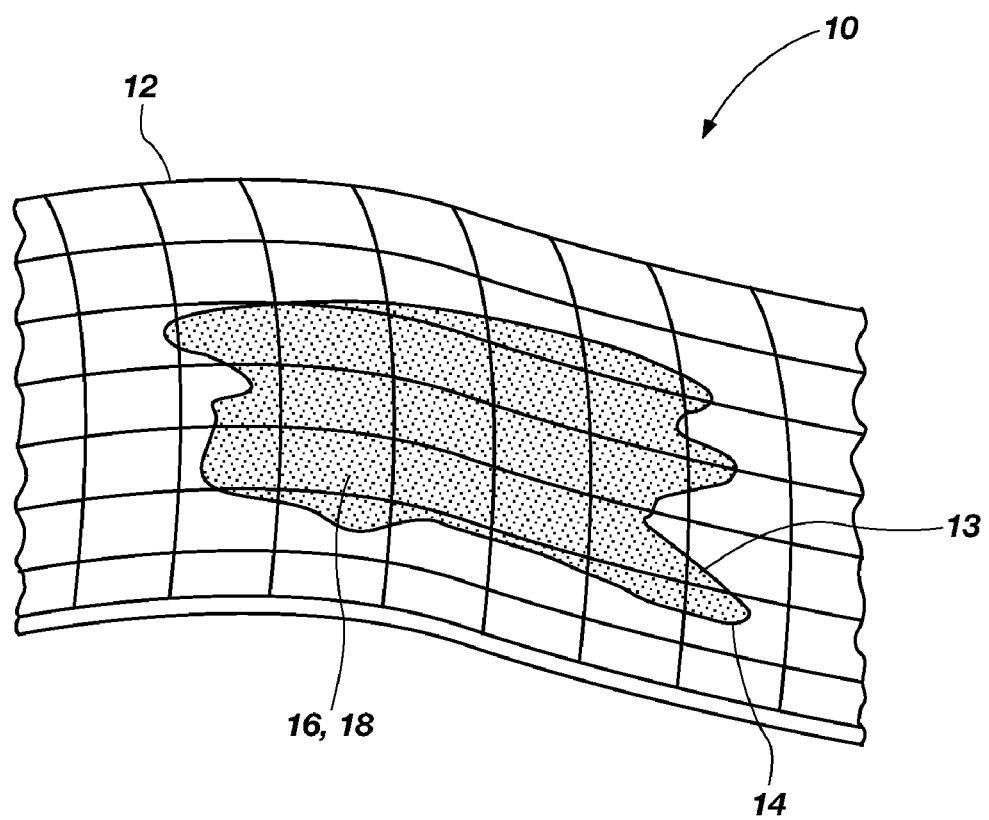
FIG. 1 comprises a perspective view of the device of the present invention.

The present invention consists of a pharmaceutical compound for the treatment of posterior retinal conditions, a device for administering the compound, and a method for using both. The pharmaceutical compound generally consists of an effective amount of a therapeutic compound and at least one means for prolonging the residence time of the therapeutic compound's contact with the eye. Further, the formulation will be sufficient for increasing the transport of the therapeutic compound across the sclera of an eye toward and into a posterior retinal region, wherein the drug formulation increases the efficiency and efficacy of delivery of the compound to the back of an eye.

Common therapeutic agents that can be utilized with the present invention include steroids, antibacterials, antivirals, antifungals, antimetabolites, VEGF inhibitors, ICAM inhibitors, antibodies, protein kinase C inhibitors, chemotherapeutic agents, neuroprotective agents, nucleic acid derivatives, aptamers, proteins, enzymes, peptides, polypeptides, immunosuppressive agents, mast cell stabilizing agents, and mycophenolate mofetil, among others or any combination thereof.

In one preferred embodiment, the compound will exhibit enhanced flux over pure topical administration because of decreased pre-scleral clearance or binding and decreased shunting into the systemic vasculature. A second preferred embodiment is one that increases the retention in the globes interior by decreasing clearance through humor dynamics or clearance into the choroidal and retinal vasculature. For example, because pre-retinal clearance is a function of conjunctival and choroidal blood flow, a vasoconstrictor can be administered to the eye to, in turn, reduce the vascular blood flow of the conjunctiva and therefore enhance drug transport into the eye. Vasoconstrictors are well known in the art and can include α-agonists such as naphazoline and tetrahydrozoline, sympathomimetics, and sympathomimetic amines selected from the group consisting of phynylethylamine, epinephire, norepinephrine, dopamine, dobutamine, colterol, ethylnorepinephrine, isoproterenol, isoetharine, metaproterenol, terbutaline, metaraminol, phenylephrine, tyramine, hydroxyamphetamine, ritrodrine, prenalterol, methoxamine, albuterol, amphetamine, methamphetamine, benzphetamine, ephedrine, phenylpropanolamine, methentermine, phentermine, fenfluramine, propylhexedrine, diethylpropion, phenmetrazine, and phendimetrazine or any combination thereof.

Alternatively, the pharmaceutical compound can be retained within the eye by combining it with an encapsulating agent that encapsulates the therapeutic agent so as to retard the clearance of the therapeutic agent. Common encapsulating agents include liposomes, micelles, microemulsions, nanoparticles, and cyclodextrins. Another effect of these encapsulating agents is to decrease degradation of the therapeutic agent in the extraocular space by inhibiting metabolism by lacrimal enzymes and binding to lacrimal proteins. Still another effect of these agents are to help sustain the therapeutic agent within a portion of the eye, as they help to form an intimate contact with at least a portion of an ocular tissue. Still another effect of these agents is to extend the absorption time of the therapeutic agent within an eye by providing a biochemical shell for controlling the exposure of the therapeutic agent to ocular fluids. Finally, encapsulating the therapeutic compound in an encapsulating agent additionally increases transscleral and transconjunctival transport.

Preferably, the above-discussed pharmaceutical composition is delivered to the eye in an ophthalmic device for the topical delivery of a therapeutic compound. Such a device preferably includes a fluid retaining member that contains a pharmaceutical formulation containing a releasable therapeutic drug for treating posterior ocular pathologies. Such a device preferably includes at least one means for prolonging the residence time of the therapeutic compound within the eye and a means for increasing the transport of the therapeutic compound across the conjunctiva and sclera toward and into a posterior ocular region. The pharmaceutical formulation preferably comprises the same compound discussed above.

In a preferred embodiment, the fluid retaining member additionally comprises a rate-limiting membrane that controls the rate of delivery of the therapeutic agent out of the housing and into an eye. Additionally, it is preferred that the fluid retaining member comprises a flexible seal circumferentially surrounding a reservoir for retaining the therapeutic compound, wherein the flexible seal creates a fluid-tight barrier when placed into contact with a surface of an eye.

In an alternative, but preferred, embodiment, the ophthalmic device additionally includes a means for decreasing the lag-time of molecular transport through the use of an active driving force. An active driving force provides an additional motivation for driving molecules across the ocular tissues and into the posterior retinal area. Such an active driving force could comprise ultra sound or iontophoresis, for example. If iontophoresis is used, it may be used with either direct or alternating iontophoretic current. The active driving force may be applied in a constant manner, or intermittently, as needed. If intermittent application is chosen, the active driving force may be applied at regular intervals, or irregular intervals.

The application of the active driving force may further be applied solely at specific times, or for specific lengths. For example, the active driving force may be applied only at the beginning of the treatment. Alternatively, the active driving force may be applied for less than 60 minutes, less than 20 minutes, or less than 5 minutes, depending upon the desired application.

The present invention is also directed to a method for increasing the concentration of a therapeutic compound in a posterior eye region, including the steps of administering to a patient an effective amount of a therapeutic compound, at least one means for prolonging the residence time of the therapeutic compound within the extraocular space, and means for increasing the transscleral transport of the therapeutic compound into the globe's interior. Preferably, the therapeutic compound and the flux enhancer are administered concurrently, but may additionally be administered one after the other. In that case it is preferred that the therapeutic compound is administered second.

Preferably, the method further includes the step of applying a means for decreasing the lag-time of molecular transport across the tissue, wherein the lag-time decreasing means comprises the application of an active driving force.

Through the administration of a pharmaceutical compound in the above manner, several positive effects can be achieved. One preferred effect is increased concentration of the therapeutic compound in a posterior region of the patient's eye. Another preferred effect is the increased efficiency and efficacy of the treatment of intermediate and posterior ocular conditions.

DETAILED DESCRIPTION OF THE INVENTION

I. Definitions

Before describing the present invention in detail, it is to be understood that this invention is not limited to specific drug delivery systems or pharmaceutical formulations, as such may vary. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration only and is not intended to be limiting. As such, they are not to be viewed as limiting the scope of the invention as defined by the claims. Additionally, when examples are given, they are intended to be examples only and not to be restrictive.

It must be noted that, as used in this specification and the appended claims, the singular forms "a", "an" and "the" include plural referents unless the context clearly dictates otherwise. Thus, for example, reference to "a drug" includes a mixture of two or more such compounds, as well as a single compound, reference to "a vasoconstrictor" includes one or more vasoconstrictors, and the like.

In describing and claiming the present invention, the following terminology will be used in accordance with the definitions set out below.

The terms "passive delivery", "passive diffusion", "diffusion", "passive drug delivery", and "passive administration" are used herein to refer to the delivery of pharmaceutically active agents through a body surface by means of a concentration gradient existing between the drug reservoir and the inner portion of the globe. Fick's first law of diffusion governs the rate of diffusion.

The terms "active delivery" and "active drug delivery" are used herein to refer to the delivery of pharmaceutically active agents through a body surface by means of an active driving force. Such an active driving force may take the form of, for example, an iontophoretic current, or ultra sonic waves, but may also comprise any of several other functionally similar known active delivery means. The active driving force provides a motivating force, separate and apart from Fickian delivery forces, for driving an active pharmaceutical agent into and through the tissues of a patient.

The terms "eye", "globe", and "ocular tissue" are used to describe the sight organ in any organism.

The terms "back of the eye", "posterior portion of the globe", "posterior compartment", and "posterior retina" are used interchangeable and typically refer to any structure on the inner portion of the sclera that is posterior to the aqueous humor. These terms, for example, refer to the optic head, optic nerve, retina, choroid, circulatory vasculatures, lens, ciliary body, and ciliary process.

The terms "vasoconstrictor" and "ocular decongestant" refer to any compound capable of decreasing the diameter of a vascular vessel by any variety of pharmacological mechanisms. The term "vasoconstrictor" also includes a mixture or mixtures of different vasoconstrictors with similar or varying mechanisms of action.

As used herein, the "sclera" refers to an aggregation of the sclera and the episcleral that contains the conjunctiva and covers the anterior portion of the sclera, posterior to the limbus, but anterior to the superior fornix of the conjunctiva. The terms "sclera" and "episclera" are used interchangeably. Typically the patient will be human, however, the invention also finds utility on small mammals, birds, farm and other domesticated animals, as well as animals found in the wild and in zoological parks.

The term "transport," as in the "transport" of a compound of interest across a body tissue, refers to passage of the compound in the direction of external to internal movement.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The term "treatment" may also be used to refer to prophylactic administration of a drug to prevent the occurrence of a disease or damage.

The terms "drug," "compound," "active agent," "pharmaceutical composition," "pharmaceutical formulation," and "pharmacologically active agent" are used interchangeably herein to refer to any chemical compound, complex or composition, charged or uncharged, that is suitable for ocular administration and that has a beneficial biological effect, preferably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

The terms "disease," "oculopathy," "posterior ocular condition," and "ocular pathology" refer to conditions that lead to pain or discomfort to the patient or in some way compromise or jeopardize visual acuity or site for the patient. The "disease" will typically occur in the region posterior to the aqueous humor.

The terms "optional" and "optionally" mean that the subsequently described circumstance may or may not occur, so that the description includes instances where the circumstance occurs and instances where it does not. For example, recitation of an "optional" vasoconstrictor encompasses a pharmaceutical formulation that is applied either with or without a vasoconstrictor.

II. Disclosure

While this invention is susceptible of embodiment in many different forms, the drawings and detailed descriptions will show specific embodiments with the understanding that the present disclosure is to be considered as an exemplification of the principles of the invention and is not intended to limit the invention to the embodiments illustrated.

The above-mentioned difficulties with topical administration can be addressed with a therapeutic formulation to decrease the negative effects of the optical environment on drug transport. Thus, the present invention comprises both a pharmaceutical formulation, a device for administering the formulation, and a method for using the formulation.

The pharmaceutical formulation disclosed herein comprises a combination of medicaments that, together, achieve an improved pharmaceutical effect for the treatment of posterior and intermediate ocular maladies following topical application of the composition to the surface of an eye. Generally, the pharmaceutical formulation of the present invention comprises a pharmaceutically effective amount of at least one therapeutic compound in combination with means for increasing the effective delivery of the therapeutic compound to a portion of the intermediate and posterior eye regions. Through the use of the present medicament combination, posterior and intermediate ocular diseases can be treated in a more efficient and effective manner by allowing topically applied medicaments to be delivered more efficiently and to maintain their efficacy within the orbital area for a longer period of time.

The combination of medicaments disclosed herein can be utilized to treat a number of known ocular conditions, also known as oculopathies. Some common ocular conditions include age related macular degeneration, diabetic retinopathy, bacterial endophthalmitis, viral endophthalmitis, fungal endophthalmitis, bacterial retinitis, fungal retinitis, viral retinitis, eye cancers, and glioblastomas from within all parts of the eye. Additionally, a number of conditions directed to specific areas of the eye can be treated using the present pharmaceutical compound, including bacterial, viral and fungal infections of the globe's interior, posterior and intermediate uveitis, and glaucomatous degradation of the optic nerve. Of course, other known optical conditions may be treated as well, as would be known by one of ordinary skill in the art.

The above-mentioned conditions are commonly treated by a number of known therapeutic compounds, any of which could be incorporated into the present invention. For example, therapeutic compounds can include, but are not limited to steroids, antibacterials, antivirals, antifungals, antimetabolites, VEGF inhibitors, ICAM inhibitors, antibodies, protein kinase C inhibitors, chemotherapeutic agents, neuroprotective agents, nucleic acid derivatives, aptamers, proteins, enzymes, peptides, polypeptides, immunosuppressive agents, mast cell stabilizing agents and mycophenolate mofetil. One or more of these compounds may be combined, along with the means for increasing the effective delivery of that compound, in a pharmaceutically effective concentration such that delivery to and treatment of posterior oculopathies is improved.

Means for increasing the effective delivery of the therapeutic compound can be combined with one or more of the formulation strategies mentioned above to enhance the pharmaceutical effect of the formulation as a whole. Generally, effective delivery increasing means could comprise one or more compounds that are capable of prolonging the residence time of the therapeutic compound within the ocular region and increasing the transport of the therapeutic compound across the eye tissues into the posterior ocular region, or both. These formulation compounds may be chemically bonded to the therapeutic compound, or may simply be mixed with it. Additionally, the therapeutic compound and effective delivery increasing means may comprise completely separate compounds for delivery to the eye either separately or together. In any case, the effective delivery increasing means is utilized in conjunction with the therapeutic agent to deliver and/or maintain an effective amount of the therapeutic agent in the posterior regions of the globe.

One preferred embodiment of the residence time prolonging means comprises means for decreasing the clearance of the therapeutic agent out of the ocular region, both upon entering the eye tissue and from the extraocular space. Drug clearance from the ocular region is a function of drug degradation, uptake kinetics of the drug into the vasculature, and blood flow. Additionally, drug clearance may also be a function of the rate of transport of the drug across clearing blood vessels of the choroid and episcleral. Thus, the clearance decreasing means comprises one or more compounds that are capable of decreasing drug degradation, inhibiting uptake kinetics of the therapeutic compound into the vasculature, decreasing blood flow out of the ocular region, or increasing the transport rate of the drug across clearing blood vessels.

One particularly helpful category of agents that can be used to decrease the clearance from the ocular region is vasoconstricting drugs. These agents restrict the blood flow into and out of the ocular region so as to maintain any medicaments within the ocular region for a longer period of time. By administering a vasoconstrictor along with the therapeutic compound of the pharmaceutical compound, the residence time of the therapeutic compound will be increased by reducing the total blood outflow from the ocular region. The longer the pharmaceutical compound is present within the ocular region, the greater the exposure time of the posterior globe region to the therapeutic compound.

Conventional vasoconstrictors, especially those vasoconstrictors specifically configured for ophthalmic application, are well known in the art. For example, medicaments such as $\alpha$-agonists, including naphazoline and tetrahydrozoline, have been used in the past as ocular "decongestants". Similarly, sympathomimetics have been used to constrict the ocular vasculature. In a preferred embodiment of the present invention, a sympathomimetic amine is selected as a vasoconstricting compound for the present pharmaceutical compound. The sympathomimetic amine may be selected from the group consisting of phenylethylamine, epinephrine, norepinephrine, dopamine, dobutamine, colterol, ethylnorepinephrine, isoproterenol, isoetharine, metaproterenol, terbutaline, metearaminol, phenylephrine, tyramine, hydroxyamphetamine, ritrodrine, prenalterol, methoxyamine, albuterol, amphetamine, methamphetamine, benzphetamine, ephedrine, phenylpropanolamine, methentermine, phentermine, fenfluramine, propylhexedrine, diethylpropion, phenmetrazine, and phendimetrazine, among other similar medicaments.

Alternately, adding an encapsulating agent to the pharmaceutical compound could prevent or delay the clearance of the therapeutic agent. Clearance of the therapeutic agent is caused, in part, by its exposure to the clearing vasculature during transport through the conjunctiva and sclera, and its inability to remain within the vitreous after passing through the clearing vasculature. The encapsulating agent solves one or more of these problems by providing a protective shell for the therapeutic agent during Fickian transport through the ocular tissues, where the shell is large enough to prevent uptake of the pharmaceutical compound into the vasculature, yet small enough to traverse the sclera. Additionally, the encapsulating agent may provide a means to retain the therapeutic agent within the posterior region of the globe for a longer period of time.

One particular type of encapsulating agent that is preferred is liposomes. Liposomes have been studied for their advantages in controlling the rate of release of an encapsulated drug. One additional advantage, however, is that liposomes form an intimate contact with external surfaces of the eye upon contact. Thus, liposomes provide a medium for the transport of the therapeutic compound through the vasculature of the ocular region, as well as providing a means for maintaining the therapeutic compound in an effective position for delivery to the posterior globe.

An alternately preferred encapsulating agent comprises cyclodextrins and their derivatives. Cyclodextrins comprise a larger-molecule encapsulating agent of sufficient size as to prevent or impede uptake of the encapsulated therapeutic agent into the vasculature during transport of the entire compound through the ocular tissues. Thus, the cyclodextrin encapsulating agent is capable of ferrying the therapeutic compound across the vasculature so as to enable release in the deeper ocular tissues.

Alternately, another preferred embodiment of the effective delivery increasing means comprises means for increasing the transport of the therapeutic compound across the ocular tissues. By increasing the rate of transport of a topically applied medicament across scleral and conjunctival tissues, therapeutic compounds can be transported into a posterior eye region in effective concentrations before the drug is degraded or cleared into the vasculature. As was discussed above, medicaments that are applied topically to an ocular region have their transport affected in a number of different ways, including metabolism of the medicament by enzymes within the lacrimal fluid, as well as binding to lacrimal proteins thereby inactivating the medicament. Further, even if intact medicament can be transported through the outer tissues of the eye, it must pass through the clearing vasculature before it can effectively treat posterior oculopathies. The transport rate increasing means helps to prevent these problems, and in so doing, increases the effective concentration of therapeutic compound that is delivered.

A number of different pharmaceutical compounds are capable of providing solutions to the above-mentioned problems. Specifically, there are a number of compounds that act as encapsulating agents, providing a protective shell for the therapeutic agent both upon application to an optical tissue, and after transport into the eye itself. For example, liposomes and cyclodextrins, discussed above, can provide for increased protection of the therapeutic agent. Additionally, micelles and microemulsions can provide similar protections for the therapeutic agent. Still other possible encapsulating agents include nanoparticles, which have been found to be especially useful as sustained release vesicles for drugs. Any of the above-named substances can be combined with the therapeutic compound of the present invention to improve transport of the compound to the posterior region of the eye.

Preferably, the pharmaceutical compound of the present invention comprises a combination of transport increasing means and residence time prolonging means. In so doing, the benefits of, for example, an encapsulating agent combined with a vasoconstrictor enable for the maximum amount of therapeutic compound to be delivered to the posterior portion of the eye, while maintaining the compound in that location for a sufficient amount of time for efficient and effective treatment of conditions in that region. A final advantage of increased retention is a decrease frequency in treatment necessary to cure or control the malady.

The effect of the above-described pharmaceutical composition can extend beyond the increase in effective ocular treatments. One additional effect is a decrease in the potential whole-body toxicity exhibited by most therapeutics targeted for ocular deliver. In standard ocular treatment via topically administered medicament, systemically active concentrations of drugs can be detected after administration of a single drop of drug to the eye. The systemic exposure can come from numerous sources, including shunting through the clearing vasculature as well as from ingestion following nasolacrimal drainage. The present invention minimizes untoward systemic effects by controlling vascular clearance and by encapsulating the therapeutic agent so as to create a drug shuttling and sustained release vesicle. By doing so, the systemic toxicity normally associated with topically administered optical treatments can be avoided.

The pharmaceutical compound discussed above may be utilized, in operation, to treat posterior retinal conditions. Generally, the pharmaceutical compound identified above is first administered in an effective amount to a patient through topical application to a surface of a patient's eye. The pharmaceutical formulation is comprised of a therapeutic compound combined with another compound that comprises means for prolonging the residence time of the therapeutic compound in the extraocular spaces, decreasing the pre-retinal clearance, or means for increasing the rate of transscleral transport of the therapeutic compound, or a combination thereof. The two components of the compound may be administered simultaneously, or one after the other, with the therapeutic compound being preferably administered second. After application, the therapeutic compound is transferred into the eye, past the conjunctiva and sclera, and into the vitreous of the eye. Thereafter, the therapeutic agent is capable of effectively and efficiently treating posterior oculopathies. Preferably, by using the above method the overall effective concentration of the therapeutic compound in the posterior region of the eye is increased.

The pharmaceutical compound of the present invention is preferably used with an ophthalmic device for the topical delivery of the compound to an eye. As can be seen in FIG. 1, device 10 comprises a fluid retaining member 12 having a pharmaceutical formulation 13 comprising a therapeutic compound 14, and at least one of means 16 for prolonging the residence time of a therapeutic compound, and means 18 for increasing transport of a therapeutic compound across an ocular tissue. Pharmaceutical compound 13 is releasably associated with fluid retaining member 12 so that, upon application of fluid retaining member 12 to an ocular surface, an effective amount of therapeutic compound 14 is released from fluid retaining member 12 and delivered to a posterior region of the patient's eye.

Fluid retaining member 12 is shown in FIG. 1 in one preferred embodiment as a gauze pad having pharmaceutical compound 13 impregnated thereon. Alternatively, fluid retaining member 12 could comprise a patch, a sponge, a hydrogel, a porous ceramic, a silicone based membrane, or other materials familiar to one with ordinary skill in the art.

Figure 2:
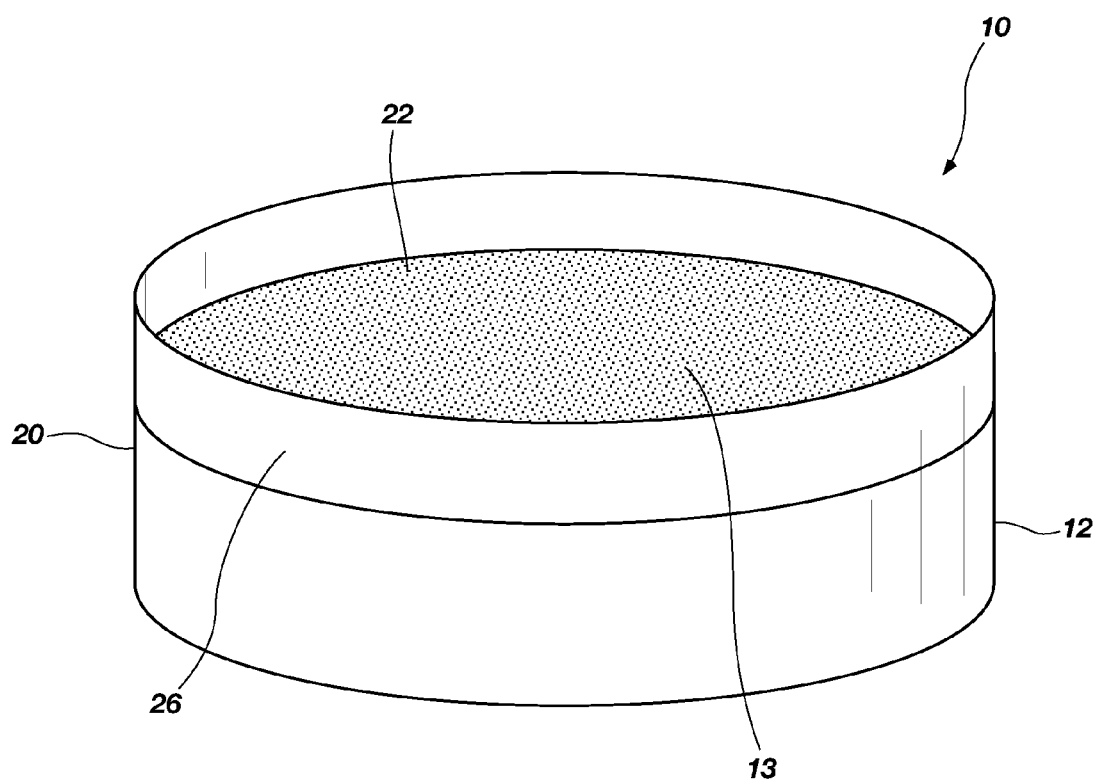
FIG. 2 comprises a perspective view of an alternative embodiment of the device.

In one preferred embodiment of the invention shown in FIG. 2, fluid retaining member 12 comprises a housing 20 having fluid reservoir 22 for retaining pharmaceutical compound 13, and seal 26 circumferentially surrounding reservoir 22. Housing 20 comprises a retention space, namely fluid reservoir 22, for retaining pharmaceutical compound 13 therein. Additionally, housing 20 can include sponge, gauze, or other similar member for the releasable retention of pharmaceutical compound 13 within fluid reservoir 22.

Surrounding reservoir 22 is seal 26, which helps to efficiently and effectively deliver medicament out of device 10 and to the posterior retinal region of an eye. Seal 26 comprises a smooth, flexible material capable of forming a fluid-tight seal against an eye of a patient upon operative placement of device 10 thereon. Preferred materials for seal 26 include silicone of varying degrees of softness. For example, Dow Q7-2218 two-part soft silicone gel, silicone and elastomer equivalents from Nusil, low durometer urethanes, and similar materials are useful in the construction of barrier element 26. It is preferred that barrier element 26 be composed of low-durometer silicone elastomeric gels. Both housing 20 and seal 26 are preferably constructed from the same materials. Alternatively, however, housing 20 may comprise a rigid or semi-rigid material to enhance secure containment of the pharmaceutical compound.

Figure 3:
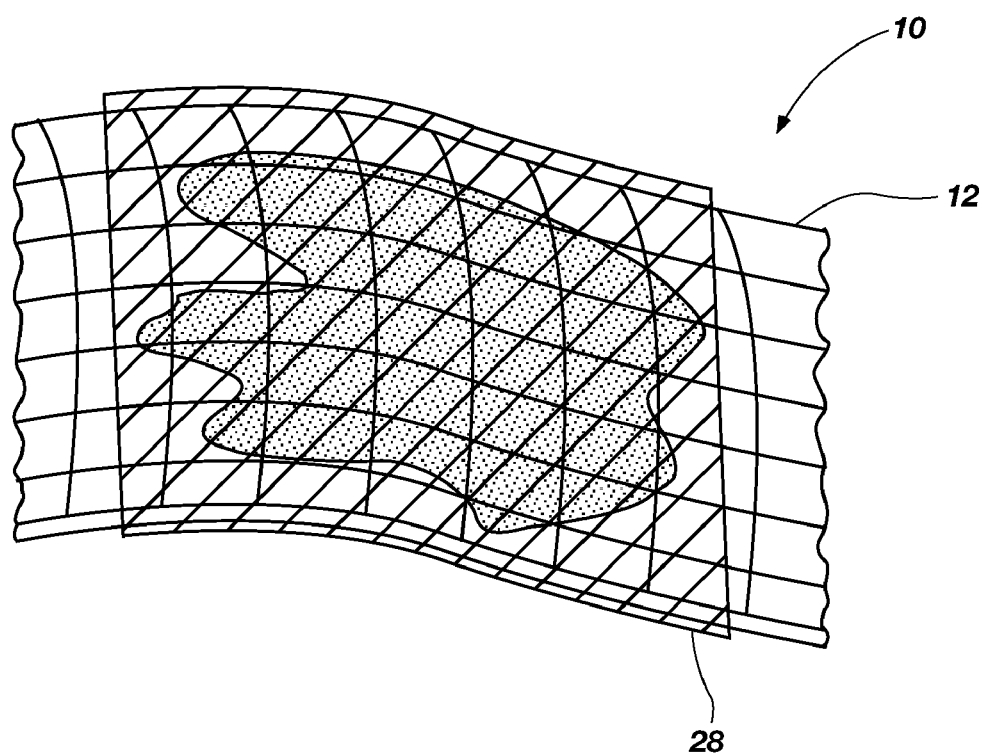
FIG. 3 comprises a perspective view of yet another alternative embodiment of the present invention.

In another preferred embodiment shown in FIG. 3, fluid retaining member 12 is associated with rate limiting membrane 28 for controlling the delivery rate of medicament out of fluid retaining member 12. As will be described further below, generally medicament that is delivered through topical application to an eye is absorbed into the eye via standard Fickian transport. Occasionally, however, a medicament will have a transport rate that is unnecessarily high, causing an overabundance of medicament to be introduced into the eye, which is wasteful and even dangerous. Rate limiting membrane 28 is associated between the medicament on fluid retaining member 12 and the eye of the patient so as to slow the transport of the medicament into the eye.

The rate limiting membranes can be either "hydrophobic" or "hydrophilic polymers". As used herein, the term "hydrophobic polymer" refers to polymers having equilibrium water content of less than about 10%. Suitable hydrophobic polymeric materials for use in the control membrane of the present invention include without limitation, polycarbonates, i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styreneacrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, epoxy resins, olefins such as polyethylene and polypropylene, porous rubber, poly(ethylene oxides) which are sufficiently cross-linked to have an equilibrium water content of less than about 10%, polyvinylpyrrolidones which are sufficiently cross-linked to have an equilibrium water content of less than about 10%, poly(vinyl alcohols) which are sufficiently cross-linked to have an equilibrium water content of less than about 10%; derivatives of polystyrene such as poly(sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers, particularly those having 1-40 weight percent vinyl acetate content, such as those described in U.S. Pat. No. 4,144,317, incorporated herein by reference, polyamides, and polyurethanes. This list is merely exemplary of the materials suited for use in this invention. A more extensive list can be found in J. R. Scott & W. J. Roff, Handbook of Common Polymers (CRC Press, 1971) and in patents disclosing suitable materials for use in manufacturing microporous membranes such as U.S. Pat. No. 3,797,494, incorporated herein by reference.

As used herein, the term "hydrophilic resin" refers to resins which are at least water wetable but not necessarily water soluble and having an equilibrium water content of greater than about 10% and preferably greater than about 20%. Suitable hydrophilic resins for use in the control membrane of the present invention include materials such as polyvinylpyrrolidone, polyethylene oxides, polyox, polyox blended with polyacrylic acid or Carbopol, cellulose derivatives such as hydroxypropyl methyl cellulose, hydroxyethyl cellulose, hydroxypropyl cellulose, pectin, starch, guar gum, locust bean gum, and the like, along with blends thereof. Particularly suitable hydrophilic materials are ion exchange resins having a degree of crosslinking providing equilibrium water content greater than about 10%. Ion exchange resins and their properties are described in The Kirk-Othmer Encyclopedia of Chemical Technology, 3rd Edition, Volume 13, pps. 678 to 705, John Wiley & Sons (1981).

Preferably, the above-described ophthalmic device 10 may be beneficially associated with a means for decreasing the lag-time of molecular transport. While the above pharmaceutical compounds are capable of prolonging the residence time, and/or enhancing the transport of the therapeutic compound, the transport of the molecules across the ocular tissues is still dictated by the laws of Fickian diffusion. Therefore, it may be beneficial in some cases to add an active delivery component to the device 10. By combining the passive delivery disclosed above with an additional, active drug delivery component, the lag time of the molecule within the first several layers of the ocular tissue can be decreased, thus improving the delivery of the molecules to the posterior retinal area.

Typically, such an active delivery component comprises an iontophoretic delivery mechanism, or an ultra sonic delivery mechanism. Iontophoresis is the use of an electric current, either alternating or direct current, to drive charged compounds from a device into the tissues of a patient. Ultra sonic delivery is the use of ultra sound waves to drive molecules into and through the tissues of a patient. Such devices are well known in the art.

The active driving force is preferably used either before or in conjunction with the normal, passive delivery operations of the device. Typically, it is beneficial to utilize the active driving force at specific times, for specific lengths of time, to enhance and benefit the passive delivery operations. For example, an active driving force could be beneficially provided at the beginning of the application of the ophthalmic device 10. By doing so, initial barriers to the normal, Fickian transport can be reduced, allowing for increased passive drug delivery throughout operation. Preferably, for example, the active driving force can be applied for a period of 1-5 minutes before the passive delivery operations have started. Additionally, applying the active driving force for limited periods of time throughout operation, such as, for example, for a period of less than 60 minutes, less than 20 minutes, or even less than 5 minutes can provide similar benefits.

In another preferred embodiment, it is contemplated that the application of the active driving force for these limited periods of time can be done in intervals also, either regularly or intermittently as may be needed. For example, an active driving force can be applied initially for 1-5 minutes, and then halted completely for a period of passive drug delivery lasting for between 1-3 hours. After the passive delivery operations, an active driving force can be applied again, and passive operations repeated. The application of the active driving force, followed by passive delivery may then be cycled continuously until treatment is completed. Alternatively, the active driving force may be used in conjunction with the passive delivery of the therapeutic agent. In any case, the combination of active and passive delivery mechanisms may improve the overall delivery of the beneficial pharmaceutical agent to the posterior retinal region of the eye.

Alternatively, it may be possible to utilize the active driving force, alone, to deliver sufficient quantities of the pharmaceutical agent to the posterior retinal regions. Preferably, such an application of active driving force would include a single, 1-5 minute application of active driving force.

In operation, the above-described device 10 is first impregnated with a sufficient amount of pharmaceutical compound 13 so as to deliver an effective amount of a therapeutic compound 14 contained within the pharmaceutical compound to a posterior region of an eye. Thereafter, device 10 is placed in operative position upon an ocular surface of a patient, whereafter the pharmaceutical compound 13 is delivered to the surface of the eye, passing through at least one of the scleral and conjunctival tissues into the interior region of the eye for effective and efficient delivery of the therapeutic compound 14 to a posterior region of the eye.

If the device 10 comprises, for example, a simple impregnated gauze pad, placement of the device 10 upon an ocular surface may be accomplished by simply placing the gauze pad upon an eye, or by securing the pad through medical tape, an eye patch, or the like. Alternatively, if device 10 instead comprises a housing 20 having a seal 26 thereon, it may be placed on the eye in any way that allows for a substantially fluid-tight seal between device 10 and the eye. Preferably, device 10 with seal 26 is placed between the eyelid and the eye of the patient, securing device 10 in place. Other surface applications, however, are similarly contemplated.

Once the seal 26 is in operative position upon an eye, it immediately provides for improved delivery of the pharmaceutical compound 13 to the eye. Initially, once seal 26 is in operative placement, a fluid-tight barrier between device 10 and the eye is formed, sealing pharmaceutical compound 13 in, and the surrounding lacrimal fluids out. As such, by merely placing the device 10 upon the eye, pharmaceutical compound 13 can be secured within device 10, ensuring concentrated delivery, and damaging enzymes and lacrimal proteins can, for the most part, be removed from the equation. Further, by focusing the topical application of the drug to a single, specific area, the underlying vasculature to which the pharmaceutical compound 13 can be exposed is limited. Therefore, there is less of a clearing vasculature to be overcome in delivery of the compound 13 to the rear of the eye.

Either of the above embodiments may additionally include rate-limiting membrane 28. If the selected pharmaceutical compound 13 comprises an excessive rate of transport, rate-limiting membrane 28 will help to slow the Fickian transport of the compound 13 out of the device 10. Once device 10 is placed upon the eye, pharmaceutical compound 13 is passed across membrane and into an ocular tissue. As the compound 13 passes across membrane, however, the rate of transport is slowed to an acceptable rate.

Through the use of the above pharmaceutical formulations, either in combination with a delivery device or alone, the efficacy and efficiency of medicament delivery to the posterior regions of an eye is increased.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A method for increasing the concentration of a therapeutic compound in an intermediate or a posterior region of a patient's eye, comprising:
    administering to the patient an effective amount of a therapeutic compound; and
    administering to the patient an α-agonist vasoconstrictor selected from the group consisting of, naphazoline, tetrahydrozoline, and a sympathomimetic amine selected from the group consisting of phenylethylamine, norepinephrine, dopamine, dobutamine, colterol, ethylnorepinephrine, isoproterenol, isoetharine, metaproterenol, terbutaline, metaraminol, tyramine, hydroxyamphetamine, ritrodrine, prenalterol, methoxamine, albuterol, amphetamine, methamphetamine, benzphetamine, ephedrine, phenylpropanolamine, methentermine, phentermine, fenfluramine, propylhexedrine, diethylpropion, phenmetrazine, phendimetrazine, and combinations thereof, wherein said α-agonist vasoconstrictor increases transport of the therapeutic compound across the sclera of an eye into the intermediate or posterior portion of the eye, and that also prolongs residence time of the therapeutic compound within the intermediate or posterior portions of the eye.

2. The method according to claim 1, wherein the α-agonist vasoconstrictor increases transport of the therapeutic compound across the sclera of the eye into an intermediate or posterior portion of the eye and reduces clearance of the therapeutic compound during administration of the therapeutic compound to the eye.

3. The method according to claim 1, wherein the therapeutic compound is selected from the group consisting of steroids, antibacterials, antivirals, antifungals, antimetabolites, VEGF inhibitors, ICAM inhibitors, antibodies, protein kinase C inhibitors, chemotherapeutic agents, neuroprotective agents, nucleic acid derivatives, aptamers, proteins, enzymes, peptides, polypeptides, immunosuppressive agents, mast cell stabilizing agents, mycophenolate mofetil, and combinations thereof.

4. The method according to claim 1, further comprising decreasing lag-time of molecular transport across the eye tissue with an active driving force.

5. The method according to claim 4 wherein the active driving force is ultra sound.

6. The method according to claim 4 wherein the active driving force is iontophoretic current.

7. The method according to claim 4 wherein the active driving force is applied constantly.

8. The method according to claim 4 wherein the active driving force is applied intermittently.

9. The method according to claim 4 wherein the active driving force is applied at regular intervals.

10. The method according to claim 4 wherein the active driving force is applied at irregular intervals.

11. The method according to claim 4 wherein the active driving force is applied only at the beginning of the treatment.

12. The method according to claim 4 wherein the length of application of the active driving force is less than 60 minutes.

13. The method according to claim 4 wherein the length of application of the active driving force is less than 20 minutes.

14. The method according to claim 4 wherein the length of application of the active driving force is less than 5 minutes.

15. The method according to claim 6 wherein the iontophoretic current is direct current.

16. The device according to claim 6 wherein the iontophoretic current is alternating current.

* * * * *